(12) United States Patent
Ameer et al.

(10) Patent No.: US 8,568,765 B2
(45) Date of Patent: Oct. 29, 2013

(54) POLY (DIOL CO-CITRATE) HYDROXYAPATITE COMPOSITE FOR TISSUE ENGINEERING AND ORTHAPAEDIC FIXATION DEVICES

(75) Inventors: Guillermo Ameer, Chicago, IL (US); Hongjin Qiu, Evanston, IL (US); Jian Yang, Arlington, TX (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/309,014

(22) Filed: Dec. 1, 2011

(65) Prior Publication Data
US 2012/0225972 A1  Sep. 6, 2012

Related U.S. Application Data

(63) Continuation of application No. 11/704,074, filed on Feb. 8, 2007, now abandoned.

(60) Provisional application No. 60/771,241, filed on Feb. 8, 2006.

(51) Int. Cl.
*A61F 2/00* (2006.01)

(52) U.S. Cl.
USPC .......................... 424/426; 424/422; 424/423

(58) Field of Classification Search
None
See application file for complete search history.

(56) References Cited

U.S. PATENT DOCUMENTS

| | | | |
|---|---|---|---|
| 5,084,051 A | 1/1992 | Tormala et al. | |
| 5,227,412 A | 7/1993 | Hyon et al. | |
| 5,993,843 A | 11/1999 | Sakurada et al. | |
| 6,159,011 A | 12/2000 | Moormann et al. | |
| 6,344,276 B1 | 2/2002 | Lin et al. | |
| 2003/0003125 A1* | 1/2003 | Nathan et al. | 424/408 |
| 2004/0230309 A1 | 11/2004 | DiMauro et al. | |
| 2004/0253203 A1* | 12/2004 | Hossainy et al. | 424/78.08 |
| 2005/0063939 A1* | 3/2005 | Ameer et al. | 424/78.37 |
| 2005/0177245 A1 | 8/2005 | Leatherbury et al. | |
| 2005/0238691 A1 | 10/2005 | Amold et al. | |
| 2005/0288481 A1 | 12/2005 | DesNoyer et al. | |
| 2007/0071796 A1 | 3/2007 | Bartholomaus | |

FOREIGN PATENT DOCUMENTS

WO  WO-2005/028631  3/2005

OTHER PUBLICATIONS

Verheyen et el. "Evaluation of hydroxylapatite/poly(L-lactide) composites: mechanical behavior", J. Biomed. Mater. Res., 26(10): pp. 1277-1296, 1992.*
Akpalu et al., Multivariable structural characterization of semicrystalline polymer blends by small-angle light scattering. *J. Polym. Sci. B Polym. Phys.*, 40: 2714-27 (2002).
Barlett et al., Measurement of particle size distribution in multilayered skin phantoms using polarized light spectroscopy. *Physical Review E.*, 65: 031906-1-031906-8 (2002).
Bordenave et al., Clinical performance of vascular grafts lined with endothelial cells. *Endothelium*, 6: 267-75 (1999).
Bos et al., Small-diameter vascular graft prostheses: Current status. *Arch. Physiol. Biochem.*, 106: 100-15 (1998).
Carnagey et al., Rapid endothelialization of PhotoFix natural biomaterial vascular grafts. *J. Biomed. Mater. Res. Part B: Appl. Biomater.*, 65B: 171-9 (2003).
Chiba et al., Mechanical responses of the periodontal ligament in the transverse section of the rat mandibular incisor at various velocities of loading in vitro. *Biomech.*, 26: 561-70 (1993).
Consigny, Endothelial cell seeding on prosthetic surfaces. *J. Long Term Eff. Med. Implants*, 10: 79-95 (2000).
Dekker et al., Adhesion of endothelial cells and adsorption of serum proteins on gas plasma-treated polytetrafluoroethylene. *Biomaterials*, 12: 130-8 (1991).
Greenwald et al., Improving vascular grafts: The importance of mechanical and haemodynamic properties. *J. Pathol.*, 190: 292-9 (2000).
Greisser et al., Growth of human cells on plasma polymers: Putative role of amine and amide groups. *J. Biomater. Sci. Polymer Edn.*, 5: 531-54 (1994).
Griffith, Polymeric biomaterials. *Acta Mater.*, 48: 263-77 (2000).
Guldberg, Consideration of mechanical factors. *Ann. N. Y. Acad. Sci.*, 961: 312-4 (2002).
Hench, Bioactive ceramics, *Ann. New York Acad. Sci*, 523: 54-71 (1988).
Hubbell et al., Endothelial cell-selective materials for tissue engineering in the vascular graft via a new receptor. *Biotechnology*, 9: 568-72 (1991).
International Search Reporting and Written Opinion for PCT/US2007/03373, dated Feb. 8, 2007.
Kikuchi et al., In vitro tests and in vivo test developed TCP/CPLA composites, *Bioceramics*, 10: 407-10 (1997).
Kim et al., Optimizing seeding and culture methods to engineer smooth muscle tissue on biodegradable polymer matrices. *Biotechnol. Bioeng.*, 57: 46-54 (1998).
Kim et al., Simultaneous measurement of angular and spectral properties of light scattering for characterization of tissue microarchitecture and its alteration in early precancer. *J. Sel. Top. Quant. Elect.*, 9: 243-56 (2003).
Kweon et al., A novel degradable polycaprolactone networks for tissue engineering. *Biomaterials*, 24: 801-8 (2003).
Langer et al., Tissue engineering. *Science*, 260: 920-6 (1993).
Lee et al., Strain rate effects on tensile failure properties of the common carotid artery and jugular veins of ferrets. *J. Biomech.*, 25: 925-7 (1992).
Li et al., Induction and morphology of hydroxyapatite, precipitated from metastable stimulated body-fluids on sol-gel prepared silica, *Biomaterials*, 14(13): 963-8 (1993).
Lisowski et al., Crystallization behavior of poly(ethylene oxide) and its blends using time-resolved wide- and small-angle x-ray scattering. *Macromolecules*, 33: 4842-9 (2000).

(Continued)

*Primary Examiner* — James Rogers
(74) *Attorney, Agent, or Firm* — Casimir Jones, S.C.

(57) ABSTRACT

The present invention is directed to a novel poly (diol citrates)-based bioceramic composite materials created using completely biodegradable and a bioceramic material polymers that may be used in implantable devices. More specifically, the specification describes methods and compositions for making and using bioceramic composites comprised of citric acid copolymers and a bioceramic material.

20 Claims, 6 Drawing Sheets

(56) References Cited

OTHER PUBLICATIONS

Misof et al., A new molecular model for collagen elasticity based on synchrotron x-ray Scattering evidence. *Biophys. J.*, 72: 1376-81 (1997).

Murphy et al., Bioinspired growth of crystalline carbonate apatite on biodegradable polymer substrata, *J. Am. Chem. Soc.*, 124(9): 1910-7 (2002).

Principles of Polymerization Odian, 3rd Ed. 1-2 (1993).

Reis et al., Bioinert and biodegradable polymeric matrix composites filled with bioactive $SiO_2$—$3CaOP_2O_5$—$MgO$ glasses and glass-ceramics, *Bioceramics*, 10: 415-8 (1997).

Szuromi et al., Preparation and analysis of cross-linked copolymers. *Macromolecules*, 33: 3993-8 (2000).

Van Wachem et al., Interation of cultured human endothelial cells with polymeric surfaces of different wettabilities. *Biomaterials*, 6: 403-8 (1985).

Van Zanten et al., Phosphatidylcholine vesicle diameter, molecular weight and wall thickness determined by static light scattering. *J. Colloid Interface Sci.*, 165: 512-8 (1994).

Vega et al., Latex particle size distribution by dynamic light scattering: Novel data processing for multiangle measurements. *J. Colloid Interface Sci.*, 261: 74-81 (2003).

Verheyen et al., Evaluation of hydroxyapatite/poly(L-lactide) composites: physico-chemical properties, *J. Mater. Sci. Mater. Med.*, 4: 58-65 (1993).

Verheyen et al., Evaluation of hydroxylapatite/poly(L-lactide) composites: mechanical behavior, *J. Biomed. Mater. Res.*, 26(10): 1277-96 (1992).

Verheyen et al., Evaluation of hydroxylapatite/poly(L-lactide) composites: an animal study on pushout strengths and interface histology, *J. Biomed. Mater. Res.*, 27(4): 433-44 (1993).

Wang et al., A tough biodegradable elastomer. *Nat. Biotech.*, 20: 602-6 (2002).

Wu et al., Preliminary report on microencapsulated islet transplantation in experimental diabetes mellitus in China. *Int. J. Pancreatol.*, 3: 91-100 (1988).

Xue et al., Biomaterial in the development and future of vascular grafts. *J. Vas. Surg.*, 37: 472-80 (2003).

Yang et al., Enhanced cell affinity of poly (D,L-lactide) by combining plasma treatment with collagen anchorage. *Biomaterials*, 23: 2607-14 (2002).

Yang et al., Fabrication and surface modification of macroporous poly (L-lactic acid) and poly (L-lactic-co-glycolic acid) (70/30) cell scaffolds for human skin fibroblast cell culture. *J. Biomed. Mater. Res.*, 62: 438-46 (2002).

Yang et al., Novel citric acid-based biodegradable elastomers for tissue engineering. *Adv. Mat.*, 16: 511-6 (2004).

Yang et al., Synthesis and evaluation of poly(diol citrate) biodegradable elastomers, *Biomaterials*, 27(9): 1889-98 (2006).

Zhang et al., Porous poly(L-lactic acid)/apatite composites created by biometric process, *J. Biomed. Mater. Res.*, 45(4): 285-93 (1999).

Ziegler et al., Tissue engineering a blood vessel: Regulation of vascular biology by mechanical stresses. *J. Cell Biochem.*, 56: 204-9 (1994).

\* cited by examiner

POLY (DIOL CO-CITRATE) HYDROXYAPATITE COMPOSITE FOR TISSUE ENGINEERING AND ORTHAPAEDIC FIXATION DEVICES

The present application claims benefit of U.S. Provisional Application No. 60/771,241 filed Feb. 8, 2006. The entire text of the aforementioned application is incorporated herein by reference.

FIELD OF THE INVENTION

The present invention describes new composites for use in orthopedic devices.

BACKGROUND

Orthopaedic, cranio-facial, and oral-maxillofacial surgeons often use tissue fixation devices such as pins, plates, and screws that are made from poly-l-lactide (PLLA), a biodegradable polymer [1-7]. Although biodegradable devices can have significant advantages over their metal counterparts, there are concerns with their use. These include slow degradation, which can be as long as 5 years, and their inability to fully integrate with bone, which can be a problem for revision surgeries [8, 9]. Also, PLLA bone screws can fracture during the fixation procedure. A strategy to improve the osteointegration capacity of PLLA has been to blend it with hydroxyapatite (HA), a bioceramic that can be found in natural bone mineral. Although HA is very brittle and hard to process into fixation devices of sufficient strength and fatigue resistance, it can impart osteoconductivity to polymers [10, 11]. Researchers have shown that under certain conditions, addition of HA particles can improve the mechanical properties of the polymer component when used in a composite blend [12-14]. Therefore composites of polymers with bioceramics may be a suitable compromise to meet mechanical property requirements and achieve osteointegration of the implant. Nevertheless, there remains a significant problem in that the PLLA continues to slowly degrade over a period of time. Moreover, incorporation of more than about 30 wt. % of HA into any such composite leads to a material that is too brittle for use in implantable devices. Thus, there remains a need for composite materials that are biocompatible, can be easily processed and will fully integrate with the surrounding bone and tissue within a year of implantation.

SUMMARY OF THE INVENTION

The present invention provides a composition comprising a composite of a citric acid polyester having the generic formula (A-B-C)n, wherein A is a linear aliphatic dihydroxy monomer; B is citric acid, C is a linear aliphatic dihydroxy monomer, and n is an integer greater than 1; and a bioceramic used for implantable tissue devices, wherein less than 75 wt. % weight ratio of said composition comprises said bioceramic. In other embodiments, at least 30 wt. % weight ratio of said composition comprises said bioceramic. In specific and alternative embodiments, the bioceramic component forms about 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, 95 wt. %, or greater than 95 wt. % of the composition.

Preferred compositions are those in which A is a linear diol comprising between about 2 and about 20 carbons. In other preferred compositions, C is a linear diol comprising between about 2 and about 20 carbons. In still other preferred compositions, both A and C are the same linear diol. In alternative embodiments, A and C are different linear diols. In specific compositions, the linear diol is 1,8-octanediol.

In exemplary embodiments, the linear aliphatic dihydroxy poly 1,8-octanediol co-citric acid. In still other exemplary embodiments, the linear aliphatic dihydroxy poly 1,10-decanediol co-citric acid.

The bioceramic may be any ceramic typically used in medical applications. For example, exemplary such bioceramics may be selected from the group consisting of calcium phosphate bioceramics, alumina-based bioceramics; zirconia-based bioceramics; silica-based bioceramics, and pyrolytic carbon-based bioceramics. Combinations of bioceramics may be used. In certain preferred embodiments, the bioceramic is a calcium phosphate bioceramic at a weight percentage of from 30 wt. % to about 75 wt. % of the total weight of the composition. In other embodiments, the bioceramic is hydroxyapatite (HA) at a weight percentage of between about 40 wt. %±5 wt. % to about 70 wt. %±5 wt. % HA to 35 wt. %±5 wt. % to about 25 wt. %±5 wt. % citric acid polyester.

The compositions of the invention are such that they produce composites of preferred bending strength. In preferred embodiments, the composite has a bending strength of from about 33.9 to about 41.4 MPa. In still other preferred embodiments, the composites have a preferred compression strength, wherein the compression strength is preferably from about 32 to about 75 MPa. The composites alternatively or in addition may have a defined tensile strength in the range of from about 6 to about 10 MPa. The composites also may be characterized according to their shear strength. The preferred shear strength of the composites is between about 23 to about 28 MPa. The composites may be defined according to their bending modulus. The bending modulus is preferably from about 0.275 to about 0.502 GPa. In other embodiments, the composites are characterized by having a compression modulus of from about 0.19 to about 0.45 GPa. In still other embodiments, the composites may be characterized by a tensile modulus of from about 0.02 to about 0.34 GPa. The composites of the invention may advantageously be characterized by one or more of these features.

In addition, the invention contemplates composites of the invention which in addition to the citric acid polyester and bioceramic further comprise a polymer selected from the group consisting of poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), and polyester amide.

In specific embodiments, the composition is molded into an orthopedic fixation device. Preferred such devices include but are not limited to bone screws, bone pins, bone rods, and bone plates.

Also contemplated herein is an artificial bone, wherein said bone is comprised of a composite of the present invention.

Another aspect of the invention describes a substrate for use in an implantable device comprising a composite of the invention prepared, molded or fabricated into an orthopedic fixation device or an artificial bone structure. In preferred embodiments, the substrate further comprises a surface modification to facilitate implantation of said device with a decreased risk of implant rejection.

Also provided herein is a method of producing an implantable device, comprising: preparing a composition according to the present invention and molding the composition into an orthopedic fixation device or an artificial bone for implantation. Such a method may be used in the preparation of a bone screw, a bone pin, and a bone plate.

Also provided herein is an implantable device comprising a polymer composition of the present invention.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

DESCRIPTION OF THE PREFERRED EMBODIMENTS

In co-pending applications 60/721,687 and PCT/US2004/030631, (each incorporated herein by reference in its entirety) there is described the synthesis and characterization of elastomeric and biodegradable polyesters, referred to as poly (diol citrates (POC); see PCT/US2004/030631) and composites comprising POC with a second polymer (see U.S. 60/721, 687 and applications depending therefrom). The mechanical properties and degradation rates of POC polymers can be controlled with synthesis conditions of the polycondensation reaction and choice of diol, and their preparation does not involve any harsh solvents or exogenous catalysts [15, 16]. Furthermore, poly (diol citrates) can be very inexpensive, relative to poly (α-hydroxy acid) biodegradable polymers.

Figure 6:
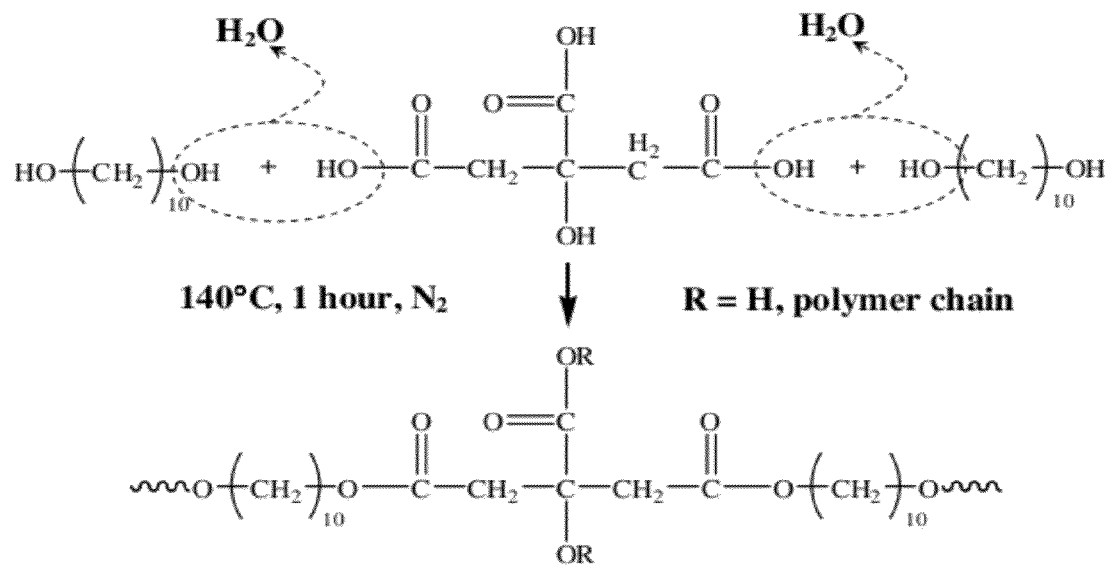
FIG. 6 is a schematic representation of the synthesis of poly (1,8-octanediol-co-citric acid).

In the present invention, it is shown that a composite of a poly (diol citrate) with HA would have the desired characteristics of a bioceramic with improved processability, mechanical properties, and degradation characteristics. Poly (1,8-octanediol-co-citrate) (POC; the production of which is shown in FIG. 6) was selected for the preparation of exemplary composites of the present invention because of its faster degradation rate (a few months to 1 year) than PLLA (3-5 years) and because its mechanical properties can be tailored by simply changing reaction conditions such as reaction temperature and time, and the ratio of 1,8-octanediol to citric acid [15, 16]. POC has also been shown to be biocompatible and could potentially enhance the biointegration of the surrounding soft tissue as in the case of fixation of a ligament graft [15, 16]. Moreover, these materials are inexpensive and easy to synthesize, an additional advantage for clinical application.

In preferred embodiments composites are prepared from POC. The methodology that was used to post-polymerize the materials is unique. Polycondensation of POC can be conducted under no vacuum, no catalyst, and low reaction temperature (under 100° C., such as 60° C., 80° C., even as low as 37° C.). Catalyst and high temperature could also be applied if needed.

The present invention shows that the POC-HA composites have the desired mechanical, degradation, mineralization, and cell compatibility characteristics to serve as compositions for implantable devices such as orthopedic fixation devices as well as to serve as compositions for use in the production of artificial bone structures. The feasibility of fabricating (i.e., molding, or machining) composite bone screws of POC-HA by compression molding and machining also is shown herein.

Compositions of poly(diol citrates) comprise a citric acid polyester having the generic formula (A-B-C)n, wherein A and C could be any of the diols or any combination of the diols; B could be citric acid, malic acid or their combinations. The diols include aliphatic diols, branched diol, cyclodiol, triol, heteroatom containing diol (such as N-methyldiethanolamine, MDEA) and macrodiol or their combinations. Any composites composed of any biodegradable elastomers (e.g. poly diol-citric acid, polyurethanes, polycaprolactone and copolymers thereof) and any bioceramic (such as HA, TCP, OCP and bioglass) with fraction from 0 to 100 wt. %, for example, 30 to 95 wt. % ceramics can be applied to fabricate fixation devices (such as pins, wires, tacks, plates, rods, screws) for clinic and cell scaffolds for tissue engineering and drug delivery.

Orthopedic fixation devices such as bone screws are often used in orthopedic, craniofacial and oral-maxillofacial surgery. The vast majority of these devices are made from metals, which can cause unwanted tissue reactions, and lead to significant bone removal if a secondary intervention is required. Alternatively, biodegradable polymers such as poly (L-lactide) (PLLA) have been used for the fabrication of some fixation devices where significant weight bearing is not an issue for the proper function of the device. Unfortunately, these devices, in particular PLLA bone screws, are not osteoconductive, have a slow degradation rate (3-5 years), can fracture during the fixation procedure, and are significantly more expensive than their metal counterparts.

One way to deal with the osteointegration deficiencies of polymers has been to blend them with bioceramics such as hydroxyapatite (HA) and tricalcium phosphate (TCP) [12-14, 22]. Bioceramics have been shown to be osteoconductive, but are brittle and hard to process into useful fixation devices for orthopaedic applications. As a result, several researchers have developed and investigated composites of HA or TCP with poly (a hydroxy acids) such as PLLA. Studies have found such composites to osteointegrate more readily than the pure polymer, supporting the further study of HA/polymer composites. Nevertheless, the polymer component remains a relatively large percentage of the composites, typically 70 wt. %, and in the case of PLLA that is used commercially, the time to total degradation after its function has been completed is still too long.

As shown in the Examples herein below, the novel bioceramic composites, based on poly (diol citrates), have enhanced osteointegration potential relative to current biodegradable fixation devices. In the present invention it is shown that it is possible to prepare bone screws and other orthopedic fixation devices that consist mostly of the bioceramic component. This maximizes the osteointegration while employing a degradable and relatively inexpensive elastomer as the macrophase binder. The inventors showed that poly (1,8-octanediol co-citrate) (POC), improves the processability and mechanical properties of bioceramic bone screws due to its biocompatibility, mechanical properties, controllable degradation rates (a few months to 1 year), and mild synthesis conditions [15]. An important criterion for the POC-HA composites was the ability to process samples via molding and machining methods. The Examples below demonstrate the successful synthesis of POC-HA composites with HA compositions of 40, 50, 60, and 65 wt. % that were readily molded and machined to make bone screws. While HA percentages of 70 or higher may be fabricated, those composites are not readily amenable to molding or machining and hence are less desirable, but may nonetheless be useful composites if molding is not required. An HA content below 40 wt. % resulted in composites that were too rubber-like and difficult to machine. Such composites with an HA content of less than 40 wt. % may nonetheless be useful in applications that do not require rigidity, e.g., tissue culture scaffolds and the like.

The mechanical property measurements of the POC-HA composites were within the range of values reported for biodegradable polymers and composites used or proposed for bone fixation devices [23]. Reported mechanical properties for polymers and composites have included bending, compression, tensile strengths, and shear strengths, whose values ranged from 40-412 MPa, 78-130 MPa, 0.6-290 MPa and 19-250 MPa, respectively. Reported values for bending, compression, and tensile moduli ranged from 1.6-124.4 GPa, 4.8-8.0 GPa, and 0.01-29.9 GPa, respectively [12, 23]. The POC-HA composites tested in this study had bending, compression, tensile, and shear strengths that ranged from 33.9-41.4 MPa, 32-75 MPa, 6-10 MPa, and 23-28 MPa, respectively. Bending, compression, and tensile moduli for POC-HA composites ranged from 0.275-0.502 GPa, 0.19-0.45 GPa, and 0.02-0.34 GPa, respectively. Except for the bending and compression moduli, the mechanical properties of POC-HA are comparable to those of other biomaterials proposed for bone fixation.

The mechanical properties of the POC-HA composites were increased by increasing the HA component. It is also possible to modulate the mechanical properties with the reaction conditions, i.e., reaction temperature and time, and choice of diol for the polycondensation reaction. Given the teachings of the present invention, the composites of the invention can readily be adapted for in vivo use in the intended application. The polymer-HA composites are expected to integrate with bone. It is contemplated that the mass percent and rate of degradation of the polymer component are parameters that may influence the function and in vivo integration of the composite. POC samples that were synthesized under the same conditions as the synthesis of the POC-HA composites lost 46 wt. % of their mass in 3 months. Further, POC when not combined with HA has previously been shown to completely degrade within 6 months when incubated in PBS at 37° C. [15]. Without being bound by any theory or mechanism of action, it is possible that the lower degradation rates reported for the POC-HA composites may be due to differing extents of the polycondensation reaction due to the lower mass percentages of polymer and the presence of thermally conductive HA particles. Both of those parameters are expected to affect the degree of cross-linking relative to pure POC for the same reaction temperature and time. Furthermore, it is also possible for the POC to covalently react with OH groups on the HA particles effectively crosslinking the POC-HA matrix [24-26]. HA would also serve as a buffer to the acidic functional groups and products generated from POC degradation, minimizing any autohydrolytic effect on degradation. Further, the degradation of the POC component can be significantly increased by "doping" with glycerol or N-methyldiethanolamine (MDEA) [16].

In vivo, HA has been shown to induce the deposition of calcium phosphate mineral on the surface of ceramic implants and bond to bone [27, 28]. The capacity of POC and POC-HA to mineralize was assessed in vitro using a modified simulated body fluid solution. Based on the SEM and EDX analysis, POC-HA composites with 40-65 wt. % HA in SBF successfully induced surface mineralization. The mineralization process involved a nucleation phase and a growth phase as evidenced by the complete coverage of the samples after 15 days of incubation in SBF [20]. However, POC was not conducive to mineralization. The apatite or calcium phosphate mineral deposition [29] may contribute to improved bone bonding in vivo and help fill in any void volumes or pores left behind by degraded POC. Depending on which bioceramic is chosen for a final application, most of the mass of the screw is expected to be integrated (when the bioceramic is an HA-type ceramic) or remodeled (when the bioceramic a TCP-type ceramic) by bone tissue and the remaining POC should be totally degraded within 2 years of implantation.

POC has been shown to be compatible (i.e. as per cell adhesion, proliferation, and differentiation assays) with several cell types including human and pig endothelial cells, human and pig smooth muscle cells, bovine chondrocytes, and bovine fibroblasts [16, 30]. It was also shown to be biocompatible in vivo in a rat subcutaneous implantation model [15]. In the present invention, the favorable cell adhesion and spreading characteristics of POC and POC-HA composites were confirmed in vitro with the use of primary human osteoblasts. The cells adhered and formed a confluent monolayer on all of the POC-HA composites evaluated (40, 50, 60, and 65 wt. % HA) (see e.g. FIG. 5) providing evidence that the composites of the present invention will be readily biocompatible in vivo. Such determinations may further be corroborated using a bone defect model.

From the above discussion, it is readily apparent that POC-HA composites can be fabricated and molded into a variety of orthopedic fixation devices. For example, POC-HA bone screws with an HA content of 65 wt. % were successfully prepared. It will readily be apparent that these compositions provide tremendous advantages over the existing technologies. Advantages of such POC-bioceramic composites include one or more of the following: a) simple synthesis and in-situ crosslinking polymerization at relatively mild temperatures while avoiding the use of exogenous catalysts and toxic solvents, b) incorporation of a high percentage of the bioceramic component, potentially enhancing osteointegration, 3) a polymer component that should degrade completely within two years rather than three to five years as in the case with PLLA, and 4) decreased cost relative to the use of poly (α-hydroxyl acids) such as PLLA. Moreover, the mechanical properties of POC-HA composites can be adjusted with the percent of HA in the composite and the material's surface supported mineralization and osteoblast adhesion and proliferation. The bioceramic particle size can be readily adjusted and its effects on mechanical properties and in vivo bone integration characteristics of the composite can be readily assessed.

In support of the above discussion, the following discussion provides a further brief explanation of exemplary individual components of the composites. Poly(diol citrates) are a family of biodegradable and biocompatible elastomers that have shown significant potential for soft tissue engineering, see e.g., U.S. patent application see U.S. 60/721,687 and applications depending therefrom. However, while those prior compositions are useful in the production of matrices for tissue culture and implantable tissue patches, those compositions are of insufficient rigidity to serve in orthopedic indications. It is desirable to increase the strength and stiffness of those composites in order to serve orthopedic purposes. The methods of the present invention are directed to strengthening such POC based polymers. Methods and compositions for preparing POC are described in detail in PCT/US2004/030631 and U.S. 60/721,687.

As noted herein, the POC is strengthened and stiffened for use in orthopedic applications by incorporating bioceramics into the POC-based elastomeric matrix. "Bioceramics" materials typically are made of inorganic salts that include the ions of calcium and phosphate, or in other examples include sulfate and carbonate. Bioceramics fulfill a unique function as biomedical materials and are used in a wide variety of applications in the human body.

Preferably, the bioceramics useful in the invention are substantially non-toxic, biodegradable, bioerodable, and bioresorbable. The terms "biodegradable" and "bioerodable" as used herein similarly refer to a material property where biological, biochemical, metabolic processes, and the like may effect the erosion or degradation of the material over time. Such degradation or erosion is due, at least in part, to contact with substances found in the surrounding tissues, body fluids, and cells, or via cellular action, enzymatic action, hydrolytic processes, and other similar mechanisms in the body. The term "bioresorbable" as used herein refers to materials that are used by, resorbed into, or are otherwise eliminated from the body of the patient via existing biochemical pathways and biological processes. For example, in embodiments where the bioceramic comprises calcium phosphate, bioresorbed calcium phosphate may be redeposited as bone mineral, be otherwise reutilized within the body, or be excreted. It is understood that some materials become bioresorbable following biodegradation or bioerosion of their original state, as described above. Preferably, the biocompatible material is such that it does not elicit a substantial detrimental response in the host, including but not limited to an immune reaction, such as an inflammatory response, tissue necrosis, and the like that will have a negative effect on the patient. In the event that such a negative effect may be seen, preferably, the material may be treated with a composition that allows the host to avoid such an adverse response to the material.

Bioceramic materials typically are made of salts of alumina; zirconia; calcium phosphates; silica based glasses or glass ceramics; or pyrolytic carbons. The salts used to prepare the bioceramics and the bioceramic matrices fabricated therefrom are commercially available or are readily prepared via known procedures. Bioceramics include calcium salts of carbonate, sulfate, phosphate, and the like. Exemplary bioresorbable calcium salts effective in the composition of this invention include calcium carbonate, calcium sulfate, calcium sulfate hemihydrate, also known as plaster of Paris, and certain porous or precipitated forms of calcium phosphate, and the like. The porous bioceramic matrix may also be fabricated from any number of natural bone sources, such as autograft or allograft material, or synthetic materials that are compositionally related to natural bone.

Calcium phosphate ceramics are in general prepared by sintering more soluble calcium salts, for example $Ca(OH)_2$, $CaCO_3$, and $CaHPO_4$, with a phosphorus-containing compound such as $P_2O_5$. Such preparations of calcium phosphate ceramics are known to those of skill in the art and have been described e.g., in U.S. Pat. Nos. 3,787,900; 4,195,366; 4,322,398; 4,373,217 and 4,330,514 (each incorporated herein by reference). Exemplary calcium phosphates for use in the invention include, but are not limited to, calcium metaphosphate, dicalcium phosphate dihydrate, calcium hydrogen phosphate, tetracalcium phosphates (TCPs), heptacalcium decaphosphate, tricalcium phosphates, calcium pyrophosphate dihydrate, crystalline hydroxyapatite, poorly crystalline apatitic calcium phosphate, calcium pyrophosphate, monetite, octacalcium phosphate, and amorphous calcium phosphate.

Chemical formulae for calcium phosphate ceramics also are provided in a range of crystalline morphologies, all of which may be used in fabricating the bioceramic matrix, as described by U.S. Pat. Nos. 6,331,312 and 6,027,742. Such calcium phosphates have been described as poorly-crystalline calcium phosphate (PCA) with an apatitic structure. Other examples include tricalcium phosphate, tetracalcium phosphate and other mixed-phase or polycrystalline calcium phosphate materials reported in U.S. Pat. Nos. 4,880,610 and 5,053,312 to Constanz et al., the disclosures of which are incorporated herein by reference.

Particularly preferred bioceramics for use in the present invention include calcium phosphate apatites, such as hydroxyapatite (HA, $Ca_{10}(PO_4)_6(OH)_2$) described by R. E. Luedemann et al., Second World Congress on Biomaterials (SWCB), Washington, D.C., 1984, p. 224, fluoroapatites, tricalciumphosphates (TCP), such as Synthograft, dicalciumphosphates (DCP), and mixtures of HA and TCP, as described by E. Gruendel et al., ECB, Bologna, Italy, 1986, Abstracts, p. 5, p. 32); mixed-metal salts such as magnesium calcium phosphates, and beta-TCMP, as described by A. Ruggeri et al., Europ. Congr. on Biomaterials (ECB), Bologna, Italy, 1986, Abstracts, p. 86; aluminum oxide ceramics; bioglasses such as $SiO_2$—CaO—$Na_2O$—$P_2O_5$, e.g. Bioglass 45S ($SiO_2$ 45 wt %. CaO 24.5%, $Na_2O$ 24.5% and $P_2O.sub.5$ 6%) described by C. S. Kucheria et al., SWBC, Washington, D.C., 1984, p. 214, and glass ceramics with apatites (MgO 4.6 wt %, CaO 44.9%, $SiO_2$ 34.2%, $P_2O_5$ 16.3% and CaF 0.5%) described by T. Kokubo et al., SWBC, Washington, D.C., 1984, p. 351; bioceramics incorporating organic ions, such as citrate, as described in U.S. Pat. No. 5,149,368 to Liu et al.; and commercial materials, such as Durapatite, Calcitite, Alveograf, and Permagraft; the disclosures of which are incorporated herein by reference.

In addition to the calcium-based bioceramics, it is contemplated that bioactive glass compositions may also be used. Such bioceramics include $SiO_2$, $Na_2O$, CaO, $P_2O_5$, $Al_2O_3$, and $CaF_2$. It is appreciated that the above-described calcium salts may be used alone or may be mixed to prepare the bioceramics described herein. Alumina and Zirconia are known for their general chemical inertness and hardness. These properties are exploited for implant purposes, where it is used as an articulating surface in hip and knee joints. The ability of these materials to be polished to a high surface finish makes them ideal candidates for this wear application. Porous alumina has also been used as a bone spacer, where sections of bone have had to be removed due to disease. In this application, it acts as a scaffold for bone ingrowth. Single crystal alumina or sapphire has also been used.

Pyrolytic carbon is a bioceramic commonly used in artificial heart valves and has been the most popular material for this application for the last 30 years. Properties that make this material suitable for this application include good strength, wear, resistance and durability, and most importantly, thromboresistance, or the ability to resist blood clotting. Pyrolytic carbon is also used for small orthopaedic joints such as fingers and spinal inserts.

The POC-bioceramic materials may be prepared as porous or channeled structures. It is understood that the nature and size of these pores or channels may affect bioresorption. In certain aspects, the pores of the structure are interconnected forming an open-cell porous structure. It is understood that each of the foregoing materials may possess differing bioresorption characteristics obtainable in the treatment subject and such characteristics may be advantageously chosen via routine experimentation for particular variations of the processes and methods described herein. It is also understood that both chemical composition and crystal morphology may affect bioresorption rates. For example, bioceramics fabricated from mixtures of calcium phosphate and calcium carbonate or calcium phosphate and calcium sulfate typically undergo resorption at higher rates than bioceramics fabricated from calcium phosphate alone. Furthermore, highly crystalline bioceramics typically undergo resorption at rates slower than poorly crystalline or amorphous bioceramics.

The porous microstructure of the bioceramics may be achieved by heat consolidation or sintering of bioceramic powders in appropriate molds. The porous matrices may be macroporous or microporous. Microporous matrices typically have pores in the range from about 1 to about 100 microns in size, while macroporous matrices typically have pores in the range from about 100 to about 1000 microns in size. In certain embodiments the pore size in a given range is substantially uniform. The pores in the matrix account for the void volume thereof. Such void volume may be from about 30% to about 80%, and illustratively about 50% to about 70% of the matrix volume. The pores are typically interconnecting, and in some cases to a substantial degree. The pores may form an open-cell configuration in some embodiments. In embodiments where the void volume constitutes a substantial portion of the matrix volume, the pores are typically close together. Illustratively, adjacent pores are separated by less than 100 microns, and in other embodiments separated by less than about the average of the diameters of the adjacent pores.

In embodiments where the POC-bioceramic composites are used for the preparation of bone-replacement materials, the pores may be arranged in predetermined patterns that correspond to bone-healing or bone-remodeling patterns, Haversian systems, and other naturally-occurring patterns in bone. Commercially available bioceramic matrices include e.g., Pro Osteon 200 and Pro Osteon 500 (hydroxyapatite bone-graft substitutes having interconnected porous structures with pore sizes of 200 or 500 microns, similar to that of cancerous bone) available from Interpore International, Irvine, Calif.; Vitoss Blocks (calcium phosphate porous structure having ca. 90% porosity, with pore sizes from 1 to 1000 microns in diameter) available from Orthovita Inc., Malvern, Pa.; and synthetic porous hydroxyapatite (made by a patented foam process having controlled porosity and pore sizes) available from Hi-Por Ceramics, United Kingdom. Such compositions may readily be used in the present invention.

While the present invention is directed to production of components for orthopedic devices, it is contemplated that in addition to the bioceramic, the POC compositions also may be reinforced with a second material. For example, the POC-HA composites also may comprise a second biodegradable and biocompatible polymer. Two such polymers are poly(L-lactic acid) (PLLA) and poly(lactic-co-glycolic acid) (PLGA). These polymers are rigid and strong and have been used in many tissue engineering applications. Furthermore, the rate of degradation could be tailored to match that of the surrounding elastomeric matrix. Poly(L-lactic acid) has a degradation time of greater than two years while poly(glycolic acid) has a degradation time of 1-2 months. By changing the ratio of lactic to glycolic acid, the degradation rate could be varied from fast (1-2 months) to slow (>2 years). For tissue engineering, the rate of degradation of the polymer scaffold should match that of tissue regrowth.

The reinforcing polymer may be a biodegradable polymer or a non-biodegradable polymer, but preferably is a biodegradable polymer. Biodegradable polymers include, but are not limited to collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of $\epsilon$-caprolactone and lactide, copolymers of glycolide and $\epsilon$-caprolactone, copolymers of lactide and 1,4-dioxane-2-one, polymers and copolymers that include one or more of the residue units of the monomers D-lactide, L-lactide, D,L-lactide, glycolide, $\epsilon$-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids). The biodegradable polymers used herein may be copolymers of the above polymers as well as blends and combinations of the above polymers. (see generally, Blum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

In particular preferred embodiments, the biodegradable or resorbable polymer is one that is formed from one or more monomers selected from the group consisting of lactide, glycolide, $\epsilon$-caprolactone, trimethylene carbonate, 1,4-dioxan-2-one, 1,5-dioxepan-2-one, 1,4-dioxepan-2-one, hydroxyvalerate, and hydroxybutyrate. In one aspect, the polymer may include, for example, a copolymer of a lactide and a glycolide. In another aspect, the polymer includes a poly(caprolactone). In yet another aspect, the polymer includes a poly(lactic acid), poly(L-lactide)/poly(D,-L-Lactide) blends or copolymers of L-lactide and D,L-lactide. In yet another aspect, the polymer includes a copolymer of lactide and $\epsilon$-caprolactone. In yet another aspect, the polymer includes a polyester (e.g., a poly(lactide-co-glycolide). The poly(lactide-co-glycolide) may have a lactide:glycolide ratio ranges from about 20:80 to about 2:98, a lactide:glycolide ratio of about 10:90, or a lactide:glycolide ratio of about 5:95. In one aspect, the poly(lactide-co-glycolide) is poly(L-lactide-co-glycolide; see e.g., U.S. Pat. No. 6,531,146 and U.S. application No. 2004/0137033.). Other examples of biodegradable materials include polyglactin, and polyglycolic acid.

Representative examples of non-biodegradable compositions include ethylene-co-vinyl acetate copolymers, acrylic-based and methacrylic-based polymers (e.g., poly(acrylic acid), poly(methylacrylic acid), poly(methylmethacrylate), poly(hydroxyethyl methacrylate), poly(alkylcynoacrylate), poly(alkyl acrylates), poly(alkyl methacrylates)), polyolefins such as poly(ethylene) or poly(propylene), polyamides (e.g., nylon 6,6), poly(urethanes) (e.g., poly(ester urethanes), poly (ether urethanes), poly(carbonate urethanes), poly(ester-urea)), polyesters (e.g., PET, polybutyleneterephthalate, and polyhexyleneterephthalate), olyethers (poly(ethylene oxide), poly(propylene oxide), poly(ethylene oxide)-poly(propylene oxide) copolymers, diblock and triblock copolymers, poly (tetramethylene glycol)), silicone containing polymers and vinyl-based polymers (polyvinylpyrrolidone, poly(vinyl alcohol), poly(vinyl acetate phthalate), poly(styrene-co-isobutylene-co-styrene), fluorine containing polymers (fluoropolymers) such as fluorinated ethylene propylene (FEP) or polytetrafluoroethylene (e.g., expanded PTFE).

The polymers may be combinations of biodegradable and non-degradable polymers. Further examples of polymers that may be used are either anionic (e.g., alginate, carrageenin, hyaluronic acid, dextran sulfate, chondroitin sulfate, carboxymethyl dextran, caboxymethyl cellulose and poly(acrylic acid)), or cationic (e.g., chitosan, poly-1-lysine, polyethylenimine, and poly(allyl amine)) (see generally, Dunn et al., J. Applied Polymer Sci. 50:353, 1993; Cascone et al., J. Materials Sci.: Materials in Medicine 5:770, 1994; Shiraishi et al., Biol. Pharm. Bull. 16:1164, 1993; Thacharodi and Rao, Int'l J. Pharm. 120:115, 1995; Miyazaki et al., Int'l J. Pharm. 118:257, 1995). Preferred polymers (including copolymers and blends of these polymers) include poly(ethylene-co-vinyl acetate), poly(carbonate urethanes), poly(hydroxyl acids) (e.g., poly(D,L-lactic acid) oligomers and polymers, poly(L-lactic acid) oligomers and polymers, poly(D-lactic acid) oligomers and polymers, poly(glycolic acid), copolymers of lactic acid and glycolic acid, copolymers of lactide and glycolide, poly(caprolactone), copolymers of lactide or glycolide and ε-caprolactone), poly(valerolactone), poly(anhydrides), copolymers prepared from caprolactone and/or lactide and/or glycolide and/or polyethylene glycol. Methods for making POC-PLLA or PLGA or other like composites are described in U.S. 60/721,687.

The composites of the invention are load bearing and may bear loads similar in magnitude to that borne by the tissue surrounding the defect, such as a bone structure of similar dimensions, or a bone structure consisting primarily of cortical bone. The structures described herein may also possess mechanical properties similar to that of natural bone, or in particular cortical bone. These mechanical properties include, but are not limited to, tensile strength, impact resistance, Young's modulus, compression strength, sheer strength, stiffness, and the like. It is appreciated that structures described herein possessing mechanical properties similar to those exhibited by the tissue surrounding such implanted structures may favorably influence the stress-shielding effect.

While it is appreciated that the above-described composites of the invention will be fashioned into replacement bone or orthopedic fixation devices, it is also contemplated that the devices may be used as drug delivery system. Either the polymer, the bioceramic, or both may include a biologically-active agent, either singly or in combination, such that the composite structure or implant will provide a delivery system for the agent at the site at which it is implanted. Thus, the agent may advantageously be delivered to adjacent tissues or tissues proximal to the implant site. Biologically-active agents which may be used alone or in combination in the implant precursor and implant include, for example, a medicament, drug, or other suitable biologically-, physiologically-, or pharmaceutically-active substance which is capable of providing local or systemic biological, physiological, or therapeutic effect in the body of the patient. The biologically-active agent is capable of being released from the solid implanted matrix into adjacent or surrounding tissue fluids during biodegradation, bioerosion, or bioresorption of the fixation device or artificial bone made from the composites of the invention.

Incorporation of bioceramic composites of the invention supports mineralization and osteoblast adhesion and proliferation, and can potentially enhance osteointegration. In vivo bone integration characteristics of the biodegradable elastomer-bioceramic composites can be adjusted with different kinds and sizes of bioceramic. Where the composites are used in facilitating bone repair, the composites may advantageously be impregnated with an "osteogenic agent" i.e., one which promotes, induces, stimulates, generates, or otherwise effects the production of bone or the repair of bone. The presence of an osteogenic agent in the site at which the composite is placed may elicit an effect on the repair of the defect in terms of shortening the time required to repair the bone, by improving the overall quality of the repair, where such a repair is improved over situations in which such osteogenic agents are omitted, or may achieve contemporaneously both shortened repair times and improved bone quality. It is appreciated that osteogenic agents may effect bone production or repair by exploiting endogenous systems, such as by the inhibition of bone resorption.

Thus, osteogenic agents in the composites of the invention may be used to effect repair of the bone by stabilizing the defect to promote healing thereby increasing healing rate, producing a more rapid new bone ingrowth, and improving overall repair of the bone. The osteogenic agents may be synthetic molecules, drugs, or pharmaceuticals involved in, or important to, bone biology, including statins, such as lovastatin, simvastatin, atorvastatin, and the like, fluprostenol, vitamin D, estrogen, a selective estrogen receptor modifier, or a prostaglandin, such as PGE-2. Growth factors or other proteins, peptides, receptor ligands, peptide hormones, lipids, or carbohydrates involved in, or important to, bone physiology may be used, including the bone morphogenic or bone morphogenetic proteins (BMPs), such as BMP-2, BMP-7, and BMP-9, chrysalin, osteogenic growth peptide (OGP), bone cell stimulating factor (BCSF), KRX-167, NAP-52, gastric decapeptide, parathyroid hormone (PTH), a fragment of parathyroid hormone, osteopontin, osteocalcin, a fibroblast growth factor (FGF), such as basic fibroblast growth factor (bFGF) and FGF-1, osteoprotegerin ligand (OPGL), platelet-derived growth factor (PDGF), an insulin-like growth factor (IGF), such as IGF-1 and IGF-2, vascular endothelial growth factor (VEGF), transforming growth factor (TGF), such as TGF-alpha and TGF-beta, epidermal growth factor (EGF), growth and differentiation factor (GDF), such as GDF-5, GDF-6, and GDF-7, thyroid-derived chondrocyte stimulation factor (TDCSF), vitronectin, laminin, amelogenin, amelin, fragments of enamel, or dentin extracts, bone sialoprotein, and analogs and derivatives thereof.

In another embodiment the osteogenic agent is a cell or population of cells involved in, or important to, bone biology, such as pluripotent stem cells, autologous, allogenic, or xenogeneic progenitor cells, chondrocytes, adipose-derived stem cells, bone marrow cells, mesenchymal stem cells, homogenized or comminuted tissue transplants, genetically transformed cells, and the like. Bone powders, including demineralized bone powders and bone matrix, may also be used. Combinations of such cell populations providing the osteogenic agent are also contemplated herein.

The osteogenic agent may be present in the structure within the range from about 0.1% to about 30% by weight, preferably in the range from about 1% to 9% by weight.

Other agents also may be used in the composites. It is contemplated that such additives may serve to reduce barriers to repair and thus maximize the potential of the osteogenic agent. Preferably, such agents are capable of preventing infection in the host, either systemically or locally at the defect site, are contemplated as illustrative useful additives. These additives include anti-inflammatory agents, such as hydrocortisone, dexamethasone, prednisone, and the like, NSAIDS, such as acetaminophen, salicylic acid, ibuprofen, and the like, selective COX-2 enzyme inhibitors, antibacterial agents, such as penicillin, erythromycin, polymyxin B, viomycin, chloromycetin, streptomycins, cefazolin, ampicillin, azactam, tobramycin, cephalosporins, bacitracin, tetracycline, doxycycline, gentamycin, quinolines, neomycin, clindamycin, kanamycin, metronidazole, and the like, antiparasitic agents such as quinacrine, chloroquine, vidarabine, and the like, antifungal agents such as nystatin, and the like, antiviricides, particularly those effective against HIV and hepatitis, and antiviral agents such as acyclovir, ribarivin, interferons, and the like. Systemic analgesic agents such as salicylic acid, acetaminophen, ibuprofen, naproxen, piroxicam, flurbiprofen, morphine, and the like, and local anaesthetics such as cocaine, lidocaine, bupivacaine, xylocaine, benzocaine, and the like, also can be used as additives in the composites.

The composites of the present invention are used to fabricate structures for use in orthopedic applications. Such structures preferably are bone fixation devices, e.g., bone screws, pins, plates and the like. Alternatively, the structures are those that can be used for repairing bone voids, fractures, non-union fractures, periodontal defects, maxillofacial defects, arthrodesis, and the like. The composites may be fabricated into useful structures using e.g., compression molding and machining methods can be applied to fabricate any desirable shapes of fixation devices and scaffolds for orthopaedic surgery and tissue engineering. The mechanical properties and degradation of the biodegradable elastomer bioceramic composites can be adjusted with the percent and particle size (from micron to nanometer) of any bioceramics (HA, TCP, OCP and bioglass) in the composite besides ratio of diol and citric acid and post-polymerization conditions such as temperature, vacuum, and polymerization time.

In addition, structures described herein may be used as reinforcement of bone fractures, dental implants, bone implants, bone prostheses and the like. It is appreciated that structures described herein may also be generally used in conjunction with other traditional fixation, immobilization, and prosthetic methods. Fractures that may be treated by structures made from the composites of the invention include fractures of the proximal humerus, diaphyseal humerus, diaphyseal femur, trochanteric femur, and trochanteric humerus. In addition, the structures may be used in the repair of osteoporosis-induced fractures, including those that involve a crushing-type injury, such as vertebral fractures, and the like. In such fractures, the porous osteoporotic bone collapses into itself typically causing a void or bone defect at the site of the fracture, in order to achieve secure stabilization of the fracture.

The various structures that can be prepared using the composites of the invention may be fabricated by using methods known to those of skill in the art. Typically, the bone fixation devices or other structures for use in the orthopedic applications described herein may be fabricated by compression molding. Compression molding processes include transfer molding and squeeze-flow molding.

In exemplary embodiments, compression molding is used. A composite of the invention, in a machined-block form, is placed on top of a bioceramic matrix in a mold cavity. The mold is then heated to a temperature at about or above the melting temperature of the polymer. Minimal loading occurs during the heating step. Pressurization of the mold is initiated once the molten polymer is fluid enough for diffusion through the porous structure. In addition, vacuum may be optionally applied during this process to prevent degradation or hydrolysis of biocompatible polymer. It is appreciated that applying a vacuum may also facilitate the diffusion of polymer into the matrix. Exemplary molding of the composites into bone screws is further described in the examples herein below.

In other embodiments, transfer molding is used. A composite of the invention, in a machined-block form, is preheated to a temperature at about or above the melting temperature of the polymer and subsequently transferred to a preheated mold cavity containing a porous bioceramic matrix. Once the molten polymer is positioned, squeeze molding is initiated by applying a load to a plunger, thereby pressurizing the mold cavity.

In still other embodiments, flow molding is used. A porous bioceramic matrix having a small-diameter open core is used. In addition, the matrix has interconnected channels that are also connected to the open core. The channels are arranged in a substantially radial pattern when viewed in a given cross section of the matrix. The porous matrix is placed in a mold cavity and the POC material is disposed into the open core by either of the above-described methods of compression molding or transfer molding. In either case this process allows orientation of the polymer from in the matrix. Such orientation may further reinforce and favorably influence the mechanical properties of the structures described herein.

Once the POC is disposed in the porous matrix by any of the methods described herein, including compression molding, transfer molding, squeeze-flow molding, and in-situ polymerization, the polymer may be optionally crosslinked. Cross-linking may be accomplished by any of the variety of known methods, including treatment with heat or irradiation, such as X-ray radiation, gamma irradiation, electron beam radiation, and the like.

It should be understood that the composites of the invention may be provided to a practitioner as bulk material that may be shaped by the medical practitioner on site. Alternatively, various prefabricated shapes ready or near ready for implantation may be produced from the composites. Such bulk material may in the form of bars, blocks, billets, sheets, and the like. Such shapes include plates, plugs, cubes, cylinders, pins, tubes, chutes, rods, screws, including the screws described in U.S. Pat. No. 6,162,225 (bone screw fabricated from allograft bone) the disclosure of which is incorporated herein by reference, and the like. In addition, shapes that tend to mimic the overall dimensions of the bone may be made from the composites of the invention. Shapes that tend to mimic the overall dimensions of the bone are particularly useful in the repair of fractures at risk of non-union. Such bulk shapes or particularly-dimensioned shapes may be obtained by employing mold cavities possessing such dimensions. Alternatively, the particularly-dimensioned shapes may be fabricated by machining the bulk stock.

Example 1

Biodegradable Elastomeric Polymers

The compositions of the invention are based on biodegradable elastomeric polymers of poly(diol) citrate molecules.

Such molecules typically comprising a polyester network of citric acid copolymerized with a linear aliphatic di-OH monomer in which the number of carbon atoms ranges from 2 to 20. Polymer synthesis conditions for the preparation of these molecules vary from mild conditions, even at low temperature (less than 100° C.) and no vacuum, to tough conditions (high temperature and high vacuum) according the requirements for the materials properties. By changing the synthesis conditions (including, but not limited to, post-polymerization temperature, time, vacuum, the initial monomer molar ratio, and the di-OH monomer chain length) the mechanical properties of the polymer can be modulated over a wide range. This series of polymers exhibit a soft, tough, biodegradable, hydrophilic properties and excellent biocompatibility in vitro.

The poly(diol)citrate polymers used herein have a general structure of:

where A is a linear, aliphatic diol and C also is a linear aliphatic diol. B is citric acid. The citric acid co-polymers of the present invention are made up of multiples of the above formula, as defined by the integer n, which may be any integer greater than 1. It is contemplated that n may range from 1 to about 1000 or more. It is particularly contemplated that n may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more. In preferred embodiments, the compositions of poly (diol citrates) that are used to prepare the implantable medical device comprise a citric acid polyester having the generic formula $(A-B-C)_n$, wherein A and C could be any of the diols or any combination of the diols; B could be citric acid, malic acid or their combinations. The diols include linear or noon-linear aliphatic diols, branched diol, cyclodiol, triol, heteroatom containing diol (such as N-methyldiethanolamine, MDEA) and macrodiol or their combinations. Any medical device coated with any biodegradable elastomers (e.g., poly diol-citric acid, polyurethanes, polycaprolactone and copolymers thereof) is contemplated to be within the aspects of the present invention.

In preferred embodiments, the identity of "A" above is poly 1,10-decanediol and in another preferred embodiment the identity of A is 1,8-octanediol. However, it should be understood that this is merely an exemplary linear, aliphatic diol. Those of skill in the art are aware of other aliphatic alcohols that will be useful in polycondensation reactions to produce poly citric acid polymers. Exemplary such aliphatic diols include any diols of between about 2 carbons and about 20 carbons. While the diols are preferably aliphatic, linear, unsaturated diols, with the hydroxyl moiety being present at the $C_1$ and $C_x$ position (where x is the terminal carbon of the diol), it is contemplated that the diol may be an unsaturated diol in which the aliphatic chain contains one or more double bonds. The preferred identity for "C" in one embodiment is 1, 8, octanediol, however as with moiety "A," "C" may be any other aliphatic alcohols. While in specific embodiments, both A and C are both the same diol, e.g., 1,8-octanediol, it should be understood that A and C may have different carbon lengths. For example, A may be 2, 3, 4, 5, 6, 7, 8, 9, 10, 11, 12, 13, 14, 15, 16, 17, 18, 19, 20 or more carbons in length, and C may independently be 2, 3, 4, 5, 6, 7, 8, 9, 10, 11, 12, 13, 14, 15, 16, 17, 18, 19, 20 or more carbons in length. Exemplary methods for the polycondensation of the citric acid with the linear diols are provided in this Example. These materials are then used as starting materials for the composites described in Example 2.

Synthesis of Poly (1,10-decanediol-co-citric acid) (PDC)
In a typical experiment, 19.212 g citric acid and 17.428 g 1,10-decanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly (1,10-decanediol-co-citric acid). Nitrogen was introduced into the reaction system before the polymer was taken out from the reaction system.

Preparation of Poly(1,8-Octanediol-co-citric acid) (POC)
In a typical experiment, 19.212 g citric acid and 14.623 g 1,8-octanediol were added to a 250 mL three-neck round-bottom flask, fitted with an inlet adapter and an outlet adapter. The mixture was melted within 15 min by stirring at 160-165° C. in silicon oil bath, and then the temperature of the system was lowered to 140° C. The mixture was stirred for another 1 hr at 140° C. to get the pre-polymer. Nitrogen was vented throughout the above procedures. The pre-polymer was post-polymerized at 60° C., 80° C. or 120° C. with and without vacuum for predetermined time (from one day to 3 weeks depending on the temperature, with the lower temperatures requiring longer times) to achieve the Poly (1,8-octanediol-co-citric acid). Nitrogen was introduced into the reaction system before the polymer was taken out from the reaction system.

Porous scaffolds of POC (tubular and flat sheets) were prepared via a salt leaching technique as follows: POC pre-polymer was dissolved into dioxane to form 25 wt % solution, and then the sieved salt (90-120 microns) was added into pre-polymer solution to serve as a porogen. The resulting slurry was cast into a poly(tetrafluoroethylene) (PTFE) mold (square and tubular shape). After solvent evaporation for 72 h, the mold was transferred into a vacuum oven for post-polymerization. The salt in the resulting composite was leached out by successive incubations in water (produced by Milli-Q water purification system every 12 h for a total 96 h. The resulting porous scaffold was air-dried for 24 hr and then vacuum dried for another 24 hrs. The resulting scaffold was stored in a desiccator under vacuum before use. Porous scaffolds are typically preferred when cells are expected to migrate through a 3-dimensional space in order to create a tissue slice. Solid films would be used when a homogenous surface or substrate for cell growth is required such as an endothelial cell monolayer within the lumen of a vascular graft.

Using similar techniques porous scaffold of PDC or other poly (diol)citrates can be prepared. In other embodiments, biphasic scaffolds can be prepared. Biphasic scaffolds consist of an outside porous phase and an inside non-porous phase as depicted in the schematic drawing shown in FIG. 15 of PCT PCT/US2004/030631, incorporated herein by reference. The non-porous phase is expected to provide a continuous surface for EC adhesion and spreading, mechanical strength, and elasticity to the scaffold. The porous phase will facilitate the 3-D growth of smooth muscle cells. Biphasic scaffolds were fabricated via following procedures. Briefly, glass rods (~3 mm diameter) were coated with the pre-polymer solution and air dried to allow for solvent evaporation. Wall thickness of the tubes can be controlled by the number of coatings and the percent pre-polymer in the solution. The pre-coated pre-polymer was partially post-polymerized under 60° C. for 24 hr;

the pre-polymer-coated glass rod is then inserted concentrically in a tubular mold that contains a salt/pre-polymer slurry. The pre-polymer/outer-mold/glass rod system is then placed in an oven for further post-polymerization. After salt-leaching, the biphasic scaffold was then de-molded from the glass rod and freeze dried. The resulting biphasic scaffold was stored in a desiccator before use. The same materials or different materials from the above family of elastomers can be utilized for both phases of the scaffold. Other biomedical materials widely used in current research and clinical application such as polylactide (PLA), polycaptrolactone (PCL), poly(lactide-co-glycolide) (PLGA) may also be utilized for this novel scaffold design.

The thickness, degradation, and mechanical properties of the inside non-porous phase can be well controlled by choosing various pre-polymers of this family of elastomers, pre-polymer concentration, coating times and post-polymerization conditions (burst pressure can be as high as 2800 mmHg). The degradable porous phase and non-porous phases are integrated since they are formed in-situ via post-polymerization. The cell culture experiments shown in FIG. 16 confirm that both HAEC and HASMC can attach and grow well in biphasic scaffolds. The results suggest that a biphasic scaffold design based on poly(diol citrate) is a viable strategy towards the engineering of small diameter blood vessels.

Synthesis of Poly (1,6-hexanediol-co-citric acid) (PHC). In a typical experiment, 19.212 g citric acid and 11.817 g 1,6-hexanediol were added to a 250 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for a predetermined time from one day to 3 weeks, depending on the temperature, to achieve the Poly (1,6-hexanediol-co-citric acid). Nitrogen was introduced into the reaction system before the polymer was taken out from the reaction system.

Synthesis of Poly (1,12-dodecanediol-co-citric acid) PDDC. In a typical experiment, 19.212 g citric acid and 20.234 g 1,12-dodecanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly (1,12-dodecanediol-co-citric acid). Nitrogen was introduced into the reaction system before the polymer was taken out from the reaction system.

Synthesis of Poly(1,8-octanediol-co-citric acid-co-glycerol) In a typical experiment (Poly(1,8-octanediol-co-citric acid-co-1% glycerol), 23.0544 g citric acid, 16.5154 g 1,8-octanediol and 0.2167 g glycerol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for another hour at 140° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly (1,8-octanediol-co-citric acid-co-1% glycerol). Nitrogen was introduced into the reaction system before the polymer was taken out from the reaction system.

Synthesis of Poly(1,8-octanediol-citric acid-co-polyethylene oxide). In a typical experiment, 38.424 g citric acid, 14.623 g 1,8-octanediol and 40 g polyethylene oxide with molecular weight 400 (PEO400) (100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 135° C. The mixture was stirred for 2 hours at 135° C. to get the pre-polymer. Nitrogen was vented throughout the above procedures. The pre-polymer was post-polymerized at 120° C. under vacuum for predetermined time from one day to 3 days to achieve the Poly (1,8-octanediol-citric acid-co-polyethylene oxide). Nitrogen was introduced into the reaction system before the polymer was taken out from the reaction system. The molar ratios can be altered to achieve a series of polymers with different properties.

Synthesis of Poly(1,12-dodecanediol-citric acid-co-polyethylene oxide). In a typical experiment, 38.424 g citric acid, 20.234 g 1,12-dodecanediol and 40 g polyethylene oxide with molecular weight 400 (PEO400) (100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 120° C. under vacuum for predetermined time from one day to 3 days to achieve the Poly(1,12-dodecanediol-citric acid-co-polyethylene oxide). Nitrogen was introduced into the reaction system before the polymer was taken out from the reaction system. The molar ratios can be altered to achieve a series of polymers with different properties.

Synthesis of Poly(1,8-octanediol-citric acid-co-N-methyldiethanoamine) POCM. In a typical experiment, 38.424 g citric acid, 26.321 g 1,8-octanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 13520° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,8-octanediol-citric acid-co-N-methyldiethanoamine). Nitrogen was introduced into the reaction system before the polymer was taken out from the reaction system. The molar ratios can be altered to citric acid/1,8-octanediol/MDEA=1/0.95/0.05.

Synthesis of Poly(1,12-dodecanediol-citric acid-co-N-methyldiethanoamine) PDDCM. In a typical experiment, 38.424 g citric acid, 36.421 g 1,12-dodecanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,12-dodecanediol-citric acid-co-N-methyldiethanoamine). Nitrogen was introduced into the reaction system before the polymer was taken out from the reaction system. The molar ratios can be altered to citric acid/1,12-dodecanediol/MDEA=1/0.95/0.05.

Example 2

Materials and Methods Used in Preparing and Characterizing Biodegradable Elastomeric Composites Made from POC and Bioceramics Example 1 describes the production of PDC as well as a number of other poly(diol)citrate polymers. In the present Example, there are provided teachings of how to further strengthen and stiffen is the poly(diol)citrate polymers by incorporating ceramics into the elastomeric polymer matrix.

Materials and Methods

Materials: Hydroxyapatite [Mw: 502.32, Assay>90 (as Ca3 (PO4)2), 0.5%>75 um, 1.4% between 45-75 um, 98.1%<45 um] was purchased from Fluka (St. Louis, Mo., USA). 1,8-octanediol (98%) and citric acid (99.5%) were purchased from Sigma-Aldrich (St. Louis, Mo., USA). These materials were used as received. PTFE tubes were purchased from McMaster-CARR, Chicago, USA.

Sample Preparation: POC pre-polymer was synthesized according to published methods [15]. Briefly, 0.05 mol of 1.8-octandiol and 0.05 mol of citric acid were added to a 100 ml round bottom flask and exposed to a constant flow of nitrogen gas. The mixture was melted under vigorous stirring at 160-165° C. Following melting, the mixture was polymerized at 140° C. for 1 hr to create a POC pre-polymer. The POC pre-polymer was mixed with various amounts of HA particles to obtain composites of 40, 50, 60, and 65 wt. % HA by mass. Briefly, POC pre-polymer was mixed with the desired amount of HA powder and placed in PTFE dishes that were pre-warmed to 80° C. The POC-HA mixture was stirred until it became clay-like, a process that generally took 5-10 hrs depending on the HA content. The POC-HA mass was then inserted into PTFE tubes to make rods or into other PTFE molds designed to meet the dimensional requirements for sample mechanical testing protocols or in situ formation of bone screws. The POC-HA in the mold was then post-polymerized at 80° C. for 3 days followed by 120° C. under 2 Pa vacuum for 1 day.

Characterization of the mechanical properties of POC-HA composites: The following mechanical properties were measured using a Sintech mechanical tester model 20/G (Triangle Park, N.C. owned by MTS now): 1) bending strength (Sb) and modulus (Eb) according to Japanese industrial standard (JIS) K7203, 2) compression strength (Sc) and modulus (Ec) according to JIS K7208, 3) tensile strength (St) and modulus (Et) according to JIS K7113, 4) shear strength (Ss)[17] and 5) torsional strength (Ts) [18].

All rods used for the mechanical tests were polished with sandpaper before measurement. For all mechanical tests, at least 6 samples were tested and the mean values and standard deviations (SD) were calculated. The density of POC and POC-HA composites was measured using the Archimedes principle as previously described [19].

Characterization of Morphology of POC-HA Composites: SEM was used for observation of morphology. All POC-HA composites for morphology were the cross section of rods obtained by compression method.

Characterization of the In Vitro Degradation of POC-HA Composites: The degradation of POC-HA composite samples (10 mm diameter×2 mm thick) with HA percentages of 40, 50, 60, and 65 wt. % was assessed in vitro in PBS, pH 7.4, at 37° C. for up to 30 weeks under static conditions. Within the POC-HA composite, only the POC is expected to degrade when incubated in aqueous solution. For comparison purposes, the degradation of POC samples synthesized under the same conditions as the composites was also assessed. PBS was changed as necessary to ensure that the pH did not drop below 7. Prior to weighing, samples were rinsed with deionized water and dried. Mass loss was calculated by comparing the initial mass (Wo) with the mass measured at a given time point (Wt), as shown in Equation 1. The results are presented as means±standard deviation (n=4).

$$\text{Mass loss (\%)} = \frac{W_o - W_t}{W_o} \times 100 \qquad (1)$$

Mineralization of POC-HA composites: Surface mineralization of POC-HA composites was assessed in vitro using modified simulated body fluid (SBF)[20]. The SBF consisted of (mmol): $Na^+$ (142.0), $K+$ (4.0), $Mg^{2+}$ (1.5), $Ca^{2+}$ (5.0), $Cl^-$ (147), $HCO_3^-$ (4.2), $HPO_4^{2-}$ (2.0) and $SO_4^{2-}$ (0.5) with the pH adjusted to 7.2 using tris(hydroxymethyl)aminomethane [21]. Briefly, discs (10 mm diameter×2 mm thick) of POC-HA composites with HA fraction of 40, 50, 60 and 65 wt. % were immersed in 10 ml of the SBF at 37° C. for up to 15 days. Fresh SBF was added every other day to maintain the ionic concentration and pH during mineralization. The morphology of deposited calcium phosphate crystals was observed via scanning electron microscopy (SEM) (Hitachi 3500 N, EPIC, Northwestern University). The stoichiometric Ca/P molar ratio was analyzed by energy dispersive X-ray (EDX).

Evaluation of the cell compatibility of POC-HA composites: POC-HA discs (7.0 mm in diameter×2 mm thick, with 40, 50, 60, and 65 wt. % HA) were sterilized by incubation in 70% ethanol for 30 minutes, washing with sterile PBS (pH 7.4), and UV exposure for 30 minutes. After sterilization, samples were washed several times with cell culture media prior to placement in the wells of a 48-well tissue culture plate. A 40 µl volume of a suspension of human osteoblast cells (HOB) (Cambrex, Pittsburgh, Pa.) ($3 \times 10^5$ cells $mL^{-1}$) was added to each well and incubated in osteoblast growth medium (OBM and OGM SingleQuots from Cambrex) at 37° C. in humidified air and 5% CO2 for up to 14 days. The culture medium was changed every three days. Samples were fixed with 2.5% gluteraldehyde in PBS for 24 h at 4° C. The morphology of the cells on the composite samples was observed via SEM.

Statistical Methods: Data are expressed as means±standard deviation. The statistical significance was calculated using two-tail Student's t-test and analysis of variance (ANOVA) and post-hoc analysis using one-way analysis of variation (ANOVA): Newman-Keuls Multiple Comparison Test. $P<0.05$ was considered as significant differences.

Example 3

Figure 1:
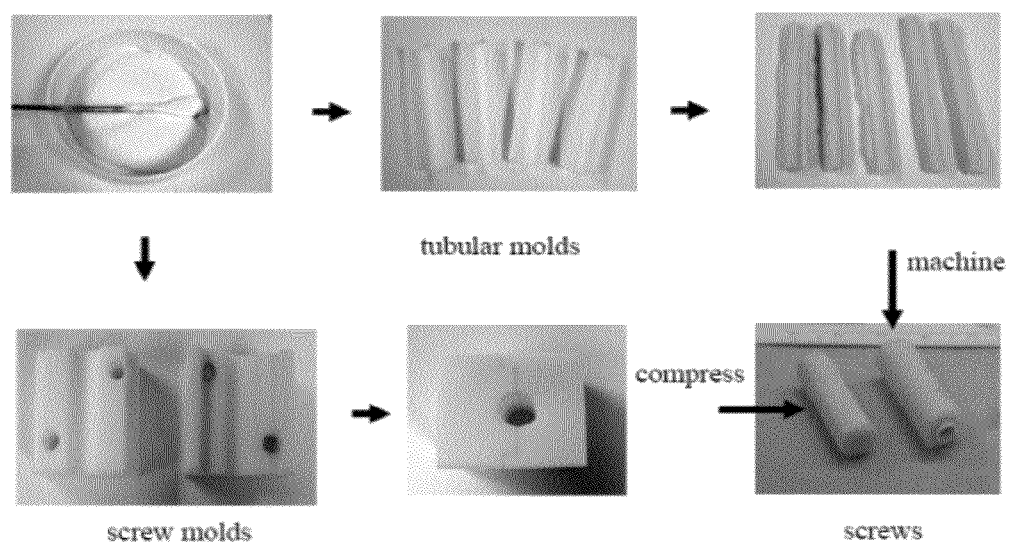
FIG. 1 Production of bone screws of POC-HA composite with 40 wt. % HA obtained by compression molding and machining methods. POC-HA composites were prepared by an in situ post-polymerization of HA and pre-POC blending at 80° C. for 3 days and 120° C. for 1 day under vacuum.

Preparation and Analysis of Bone Screws Made from Composites of POC and Bioceramics POC-HA composites having HA fraction of 40 wt. %, 50 wt. %, 60 wt. %, 65 wt. % HA were investigated for bone screws. Using compression molding method, POC-HA composites with HA from 40-65 wt. % were compressed into molds of rods and screws. The POC-HA rods obtained were strong enough to be further machined into screws. The POC-HA screws from compression molding and machining methods were shown in FIG. 1.

Characterization of the Mechanical Properties of Composites. The mechanical property measurements (bending, compression, shear, tension and torsion) are summarized in Table 1.

In summary, the POC-HA composites with 65 wt. % HA had the highest bending strength and modulus, compression strength and modulus, tensile strength and modulus, shear strength and torsional strength. Interestingly, for HA percent of 40-60 wt. % there was no statistically significant difference for most of the mechanical properties. The mechanical properties of all POC-HA composites tested were significantly increased relative to POC samples. The density of samples increased with increasing percentage of HA.

TABLE 1

Effect of HA fraction on mechanical properties of POC-HA composites

| Composite | POC-HA (Wt %) | $\rho$ (g/cm$^3$) | Sb (MPa) | Eb (MPa) | Sc (MPa) | Ec (MPa) | St (MPa) | Et (MPa) | Ss (MPa) | Ts (N.m) |
|---|---|---|---|---|---|---|---|---|---|---|
| HA 40 | 40/60 | 1.609 (±0.016) | 33.9 (±5.7) | 275 (±80) | 32.0 (±13.0) | 189 (±21) | 7.8 (±0.5) | 21.4 (±1.8) | 23.3 (±1.6) | 22.9 (±1.6) |
| HA 50 | 50/50 | 1.653 (±0.014) | 37.7 (±4.6) | 323 (±63) | 64.0 (±9.4) | 264 (±14) | 7.1 (±0.3) | 30.2 (±2.2) | 25.1 (±1.7) | 24.2 (±2.0) |
| HA 60 | 60/40 | 1.734 (±0.061) | 34.7 (±3.0) | 314 (±54) | 52.6 (±11.5) | 297 (±41) | 6.4 (±2.0) | 85.4 (±8.8) | 25.9 (±1.6) | 21.4 (±1.9) |
| HA 65 | 65/35 | 1.885 (±0.072) | 41.4 (±3.1) | 502 (±40) | 74.6 (±9.0) | 449 (±27) | 9.7 (±2.3) | 334.8 (±73.5) | 27.7 (±2.4) | 27.3 (±4.9) |

Note:
$\rho$: density;
Sb: bending strength,
Eb: bending modulus,
Ss: shear strength,
Sc: compression strength,
Ec: compression modulus,
St: tensile strength (rectangular specimens),
Et: tensile modulus,
Ts: torsional strength (1) Bending strength (Sb) and modulus (Eb): With increasing HA fraction from 40 wt. % to 65 wt. %, bending strength (Sb) increased reaching about 41 MPa at 65 wt. % which was considered as the highest one among the composites, and composites showed almost the similar Sb at 40, 50, and 60 wt. %. The bending modulus showed the similar increasing tendencies as bending strength with increasing HA fraction from 40-65 wt. %. The highest modulus is 502 MPa at 65 wt. %.

(2) Compression strength (Sc) and modulus (Ec): Compression strength (Sc) greatly increased from 32 to 75 MPa in proportion to HA fraction from 40 to 65 wt. % except for 50 wt. %. Compression modulus at 65 wt. % HA is the highest and the values for composites with 40-60 wt. % HA are similar to each other. It seems likely that it originated from the HA particle aggregating in the composites.

(3) Shear strength (Ss): The shear strength (Ss) at 65 wt. % is significantly higher than that at 40 wt. %, and there is no significant difference at 40-60 wt. %.

(4) Tensile strength (St) and modulus (Et): Compared with POC, tensile strength improved greatly for composites with fraction from 40-65 wt. %, and the composite at 65 wt. % has higher tensile strength than those at 50 wt. % and 60 wt. %. Modulus increased with increasing HA concentration from 50-65 wt. % and reached 335 MPa at 65 wt. %, the highest one among composites.

(5) Torsional strength (Tt): Torsional strength (Tt) did not change significantly with increasing HA fraction from 50-60 wt. %. Torsional strength at 65 wt. % HA is the highest.

Example 4

The Morphology and Other Properties of POC-HA Composites

Figures 2A, 2B:
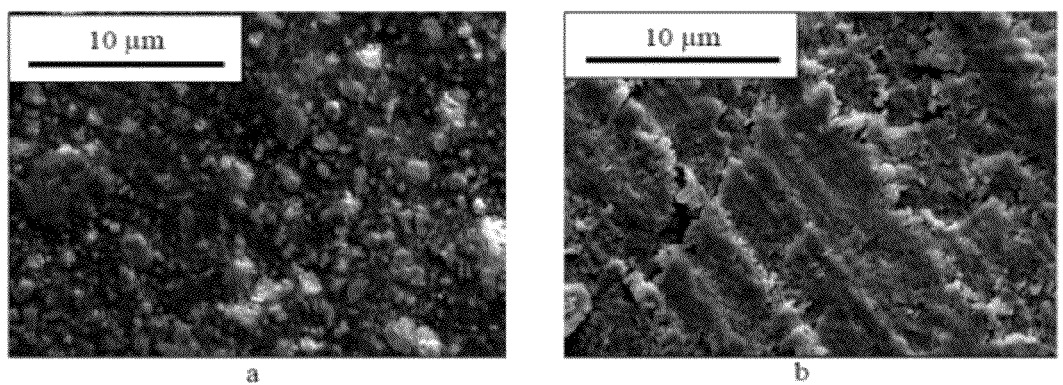
FIG. 2 SEM images of surface of POC-HA composites with a) 40 wt. % HA and b) 65 wt. % HA.

FIG. 2 showed that for the POC composite with 40 wt % HA, HA as nodules dispersed in POC-HA. However, there were continuous flakes of HA covering on the surface for the POC composite with 65 wt. % HA, indicating higher amount of HA in this composite.

Figure 3:
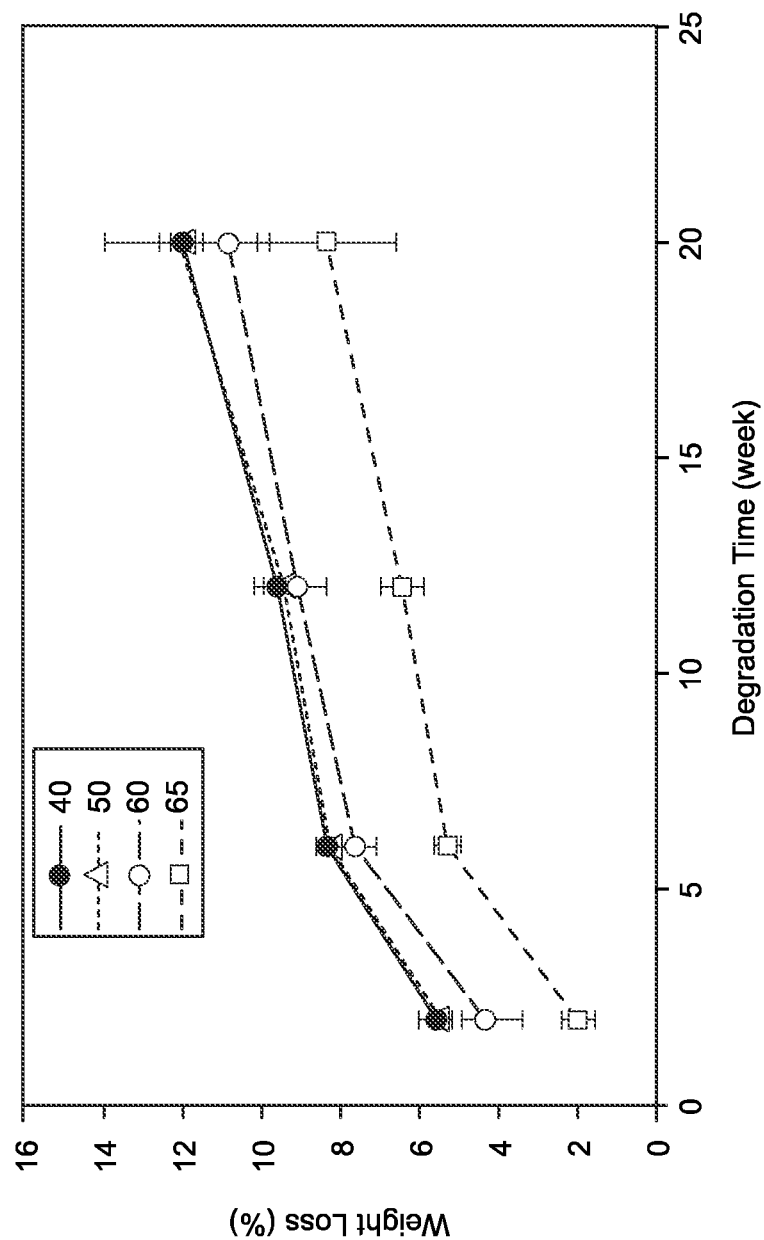
FIG. 3 Weight loss of POC-HA composites with HA fraction of 40, 50, 60, to 65 wt. % in vitro (PBS at 37° C.) at 2, 6, 12 and 20 weeks. POC-HA composites were prepared at 80° C. for 3 days and 120° C. under vacuum for 1 day FIG. 4 Mineralization in SBF for POC at a) 3 days and b) 15 days, for POC-HA with 40 wt. % HA at c) 3 days, d) 15 days, and for POC-HA with 65 wt. % HA e) 3 days and f) 15 days. Magnification of all images: ×4.5K.

In Vitro Degradation of POC-HA Composites The mass loss over time profiles for POC-HA composites incubated in PBS at 37° C. are shown in FIG. 3. Mass loss is due to the aqueous hydrolytic degradation of POC within the composite. The degradation of the POC-HA composite scaffolds with HA percentages of 40, 50, and 60 was very similar at all time points with a total mass loss of approximately 12 wt. % at 20 weeks. POC-HA composite with 65 wt. % HA had the slowest degradation rate with a mass loss of approximately 8.4 wt. % at 20 weeks. For comparison purposes, POC samples lost 46 wt. % of their mass by 12 weeks.

Figures 4A, 4B, 4C, 4D, 4E, 4F:
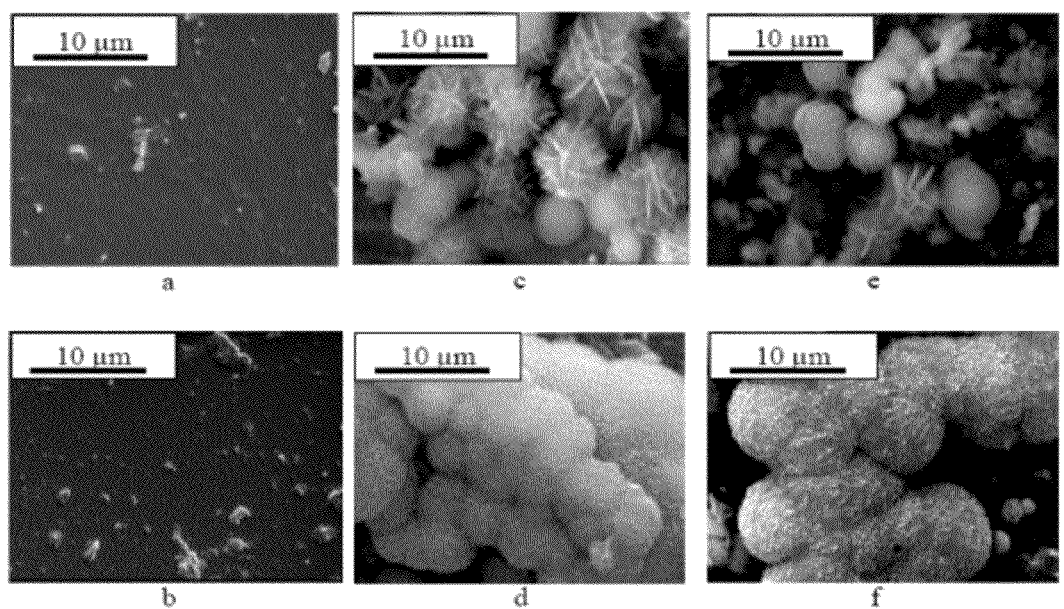

Mineralization of POC and POC-HA Composites in SBF SEM showed that mineralization was not observed on the surface of POC incubated in SBF for 3 days through 15 days as shown in FIGS. 4a and b. However, mineral nodules began to form and aggregated on the surface of composites throughout the 15 days of incubation in SBF at 37° C. (FIG. 4 c-f). Mineral nodules merged into a continuous covering on most of the sample's surface at 15 days. The composition of the mineral, in terms of the molar ratio of Ca/P, was confirmed by the EDX to be 1.5-1.7. Deposition of a large number of calcium phosphates was remarkable on the surface of composites due to exposure of HA. The osteoconductivity of POC-HA composites would be largely predicted.

Figures 5A, 5B, 5C, 5D, 5E, 5F:
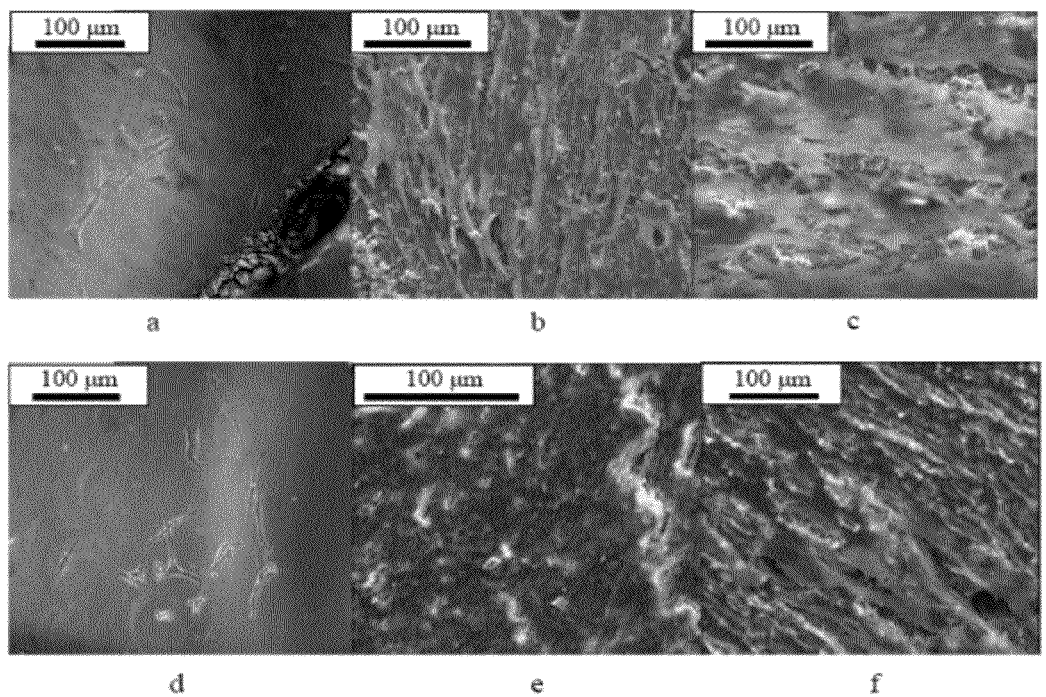
FIG. 5 LM images of POC seeded with HOB in vitro at a) 3 days b) 14 days; SEM images of POC-HA composites seeded with human osteoblasts in vitro for 40 wt. % HA at c) 3 days d) 15 days and for 65 wt. % at e) 3 days and f) 14 days.

Evaluation of the Cell Compatibility of POC-HA Composites In order to investigate whether HOB can attach and proliferate on the POC-HA composites, the morphology of cells seeded on the surface of POC and POC-HA composites with 40 wt. % and 65 wt. % HA respectively was observed by light microscopy (LM) and SEM as shown in FIG. 5. LM showed that HOB cells can attach, spread out and proliferate on the surface of POC cultured from 3 days through 14 days (FIG. 5a-b). SEM in FIGS. 5c and e showed that for both POC-HA composites cultured for 3 days, the cells attached and spread out well on the surface of both composites, and layers of the cells on the surface of 65 wt. % POC-HA composite were observed. It revealed a good covering on both composites, and better cell proliferation on 65 wt. % HA composites. While culturing up to 14 days, both surfaces were almost completely covered by layers of cells (FIG. 5 d and f). Moreover, the broken cell layers were observed on the surfaces of both materials in some area due to the thickness of the cell layers. However, HOB cells still remain round aggregating on the POC surface even culturing for 14 days.

Example 5

Further Measurements of Mechanical Properties (1) Bending strength (Sb) and modulus (Eb). (Japanese Industrial Standard (JIS) K7203 measurements were determined using a three point bending test using rods with a range of diameter from 5.0 to 6.5 mm and a length of 30 mm).

$$Sb = 8F\max L/\pi D_3$$

$$Eb = 4L_3/3\pi D_4(E/Y)$$

where Fmax=maximum force (N); L=support span (mm); D=diameter (mm); and E/Y=gradient of linear portion of stress-strain curve (N/mm).

(2) Compression strength (Sc) and modulus (Ec) (Japanese Industrial Standard (JIS) K7208 was measured using rods with a range of diameter from 5.0 to 6.5 mm and a length of 15-30 mm.

$$Sc = F\max/A$$

$$Ec = E/Y$$

where Fmax=maximum force (N); A=compressed area (mm2); E/Y=gradient of linear portion of stress-strain curve (N/mm2).

(3) Shear strength (Ss) (Measured by Suuronen's method [20] at a testing speed of 10 mm min$^{-1}$) using rods with a range of diameter from 5.0 to 6.5 mm and a length of 20 mm.

$$Ss = F\max/2A$$

where Fmax=maximum force (N); A=loading area (mm2).

(4) Tensile strength (St) and modulus (Et). (Japanese Industrial Standard (JIS) K7113 using dog bone shaped samples (26 mm×4 mm×1.6 mm) at testing speed of 10 mm/min $$St = F\max/A$$

$$Et = E/Y$$

Where Fmax=maximum force (N); A=transversal cross-sectional area (mm2); E/Y=gradient of linear portion of stress-strain curve (N/mm).

(5) Torsional strength (Ts) The test rod was installed to Sintech 20/G Materials Testing Machine, using the dumbbell shaped samples having an average diameter of 4.7 mm and length of 16.5 mm. The rotating wheel was turned at a rate of 0.4 rev/min by means of a chain attached to the load cell. The load pulling the chain was recorded and used for the calculation of the torque strength according to the equation $$Ts = 16F\max \cdot R/(\pi D3)$$

where Ts=torsion strength (MPa), Fmax=load at fracture (N), R=radius of the rotating wheel=38 mm and D=diameter of the rod (mm).

TABLE 2

Results of ANOVA on Mechanical Properties

| Number | Sb (MPa) | Eb (MPa) | Sc (MPa) | Ec (MPa) | St (MPa) | Et (MPa) | Ss (MPa) | Ts (N m) |
|---|---|---|---|---|---|---|---|---|
| HA40 vs HA50 | N S | N S | P < 0.001 | N S | N S | N S | N S | N S |
| HA40 vs HA60 | N S | N S | P < 0.05 | N S | N S | P < 0.001 | N S | N S |
| HA40 vs HA65 | P < 0.05 | P < 0.001 | P < 0.001 | P < 0.01 | N S | P < 0.001 | P < 0.01 | P < 0.05 |
| HA50 vs HA60 | N S | N S | P < 0.05 | N S | N S | P < 0.001 | N S | N S |
| HA50 vs HA65 | N S | P < 0.001 | N S | N S | P < 0.05 | P < 0.001 | N S | N S |

TABLE 2-continued

Results of ANOVA on Mechanical Properties

| Number | Sb (MPa) | Eb (MPa) | Sc (MPa) | Ec (MPa) | St (MPa) | Et (MPa) | Ss (MPa) | Ts (N m) |
|---|---|---|---|---|---|---|---|---|
| | | | | P-values | | | | |
| HA60 vs HA65 | $P < 0.05$ | $P < 0.001$ | $P < 0.01$ | $P < 0.05$ | $P < 0.01$ | $P < 0.001$ | N S | $P < 0.05$ |

Note:
Sb: bending strength,
Eb: bending modulus,
Ss: shear strength,
Sc: compression strength,
Ec: compression modulus,
St: tensile strength (rectangular specimens),
Et: tensile modulus,
Ts: torsional strength.
Tensile strength POC vs HA (40-65%): $P < 0.001$; Tensile modulus POC vs HA (60-65%): $P < 0.001$; and POC vs HA (40-50%): N S

TABLE 3

Results of ANOVA on degradation between POC-HA (40-65 wt. %) composites respectively in 2 and 20 weeks.

| Time (week) | HA40 vs HA50 | HA40 vs HA60 | HA50 vs HA60 | HA40 vs HA65 | HA50 vs HA65 | HA60 vs HA65 |
|---|---|---|---|---|---|---|
| | | | P-values | | | |
| 2 | N.S | N.S | N.S | $P < 0.01$ | $P < 0.001$ | $P < 0.001$ |
| 20 | N.S | N.S | N.S | $P < 0.05$ | $P < 0.05$ | $P < 0.01$ |

TABLE 4

Results of ANOVA on degradation of POC-HA (40-65 wt. %) composites from 2 to 20 weeks.

| Time (week) | HA40 | HA50 | HA60 | HA65 |
|---|---|---|---|---|
| | | P-values | | |
| 2 vs 6 | $P < 0.001$ | $P < 0.001$ | N.S | N.S |
| 2 vs 12 | $P < 0.001$ | $P < 0.001$ | N.S | N.S |
| 2 vs 20 | $P < 0.001$ | $P < 0.001$ | N.S | $P < 0.01$ |
| 6 vs 12 | $P < 0.05$ | $P < 0.01$ | N.S | N.S |
| 6 vs 20 | $P < 0.001$ | $P < 0.001$ | N.S | $P < 0.01$ |
| 12 vs 20 | $P < 0.01$ | $P < 0.05$ | $P < 0.05$ | $P < 0.05$ |

REFERENCES

The following references are referred to herein throughout using a numeric identifier. Each of these references is incorporated herein by reference in its entirety.

1. PU, R., *Absorbable materials in orthopaedic surgery*. Ann Med 1991. 23: p. 109-115.
2. Yamamuro, T., et al., *Bioabsorbable Osteosynthetic Implants of Ultra-High Strength Poly-LLactide—a Clinical-Study*. International Orthopaedics, 1994. 18(6): p. 332-340.
3. Habal M B, e., *The journal of craniofacial surgery*. 1997 (Pennsylvania USA: Lippincott-Raven Publishers).
4. Eppley, B. L. and A. M. Sadove, *A comparison of resorbable and metallic fixation in healing of calvarial bone grafts*. Plast Reconstr Surg, 1995. 96(2): p. 316-22.
5. Habal, M. B. and W. S. Pietrzak, *Key points in the fixation of the craniofacial skeleton with absorbable biomaterial*. Journal of Craniofacial Surgery, 1999. 10(6): p. 491-499.
6. Suuronen, R., *Biodegradable Fracture-Fixation Devices in Maxillofacial Surgery*. International Journal of Oral and Maxillofacial Surgery, 1993. 22(1): p. 50-57.
7. Eppley, B. L., *A bioabsorbable poly-L-lactide miniplate and screw system for osteosynthesis in oral and maxillofacial surgery—Discussion*. Journal of Oral and Maxillofacial Surgery, 1997. 55(9): p. 945-946.
8. Matsusue, Y., et al., *A long-term clinical study on drawn poly-L-lactide implants in orthopaedic surgery*. Journal of Long-Term Effects of Medical Implants, 1997. 7(2): p. 119-137.
9. Bergsma, J. E., et al., *Late degradation tissue response to poly(L-lactide) bone plates and screws*. Biomaterials, 1995. 16(1): p. 25-31.
10. Kikuchi M, C. S.-B., Suetsugu Y, Tanaka J, *In vitro tests and in vivo test developed TCP/CPLA composites*. Bioceramics, 1997. 10: p. 407-410.
11. Reis R L, C. A., Fernandes M H, Correia R N, *Bioinert and biodegradable polymeric matrix composites filled with bioactive SiO2-3CaOP2O5-MgO glasses and glass-ceramics*. Bioceramics, 1997. 10: p. 415-418.
12. Verheyen, C. C., et al., *Evaluation of hydroxylapatite/poly (L-lactide) composites: mechanical behavior*. J Biomed Mater Res, 1992. 26(10): p. 1277-96.
13. Verheyen C C P M, K. C., Blieckhogervorst de J M A, Wolke J G C, Blitterswijk van C A, Groot de K, *Evaluation of hydroxyapatite/poly(L-lactide) composites: physicochemical properties*. J Mater Sci Mater Med 1993. 4: p. 58-65.
14. Verheyen, C. C., et al., *Hydroxylapatite/poly(L-lactide) composites: an animal study on pushout strengths and interface histology*. J Biomed Mater Res, 1993. 27(4): p. 433-44.
15. Jian Yang, A. R. W., Guillermo A. Ameer, *Novel citric acid-based biodegradable elastomers for tissue engineering*. Adv. Mater., 2004. 16(6): p. 511-516.
16. Yang, J., et al., *Synthesis and evaluation of poly(diol citrate) biodegradable elastomers*. Biomaterials, 2006. 27(9): p. 1889-98.
17. Suuronen R, P. T., Taurio R, Törmälä P, Wessman L, Rönkkö K, Vainionpää S., *Strength retention of self-reinforced poly-L-lactide screws and plates: an in vivo and in vitro study*. J Mater Sci Mater Med 1992. 3: p. 426-431.

18. T Pohjonen, P. H., P Törmälä, K Koskikare, H Pätiälä, P Rokkanen, *Strength retention of selfreinforced poly-L-lactide screws. A comparison of compression moulded and machine cut screws.* J Mater Sci Mater Med 1997. 8: p. 311-320.
19. Yang, J., et al., *Fabrication and surface modification of macroporous poly(L-lactic acid) and poly(L-lactic-co-glycolic acid) (70/30) cell scaffolds for human skin fibroblast cell culture.* J Biomed Mater Res, 2002. 62(3): p. 438-46.
20. Zhang, R. and P. X. Ma, *Porous poly(L-lactic acid)/apatite composites created by biomimetic process.* J Biomed Mater Res, 1999. 45(4): p. 285-93.
21. Murphy, W. L. and D. J. Mooney, *Bioinspired growth of crystalline carbonate apatite on biodegradable polymer substrata.* J Am Chem Soc, 2002. 124(9): p. 1910-7.
22. Shikinami, Y. and M. Okuno, *Bioresorbable devices made of forged composites of hydroxyapatite (HA) particles and poly-L-lactide (PLLA): Part I. Basic characteristics.* Biomaterials, 1999. 20(9): p. 859-877.
23. Daniels, A. U., M. K. Chang, and K. P. Andriano, *Mechanical properties of biodegradable polymers and composites proposed for internal fixation of bone.* J Appl Biomater, 1990. 1(1): p. 57-78.
24. Behiri J C, B. M., Khorasani S, Wiwattanadate D, Bonfield W, *Advanced bone cement for longterm orthopaedic implantations* In: Bonfield W, Hastings G W, Tanner K E, editors. Bioceramics, 1991 4(Oxford: Butterworth-Heinemann, UK): p. 301-307.
25. Liu Q, D. W. J. R., Bakker D, Van Blitterswijk C A, *Surface modification of hydroxyapatite to introduce interfacial bonding with Polyactive™ 70/30 in a biodegradable composites.* J Mater Sci Mater Med., 1996. 7: p. 551-557.
26. Liu, Q., J. R. de Wijn, and C. A. van Blitterswijk, *Covalent bonding of PMMA, PBMA, and poly(HEMA) to hydroxyapatite particles.* J Biomed Mater Res, 1998. 40(2): p. 257-63.
27. L L, H., *Bioactive ceramics.* Ann. New York Acad Sci 1988. 523: p. 54-71.
28. Li, P. J., et al., *Induction and Morphology of Hydroxyapatite, Precipitated from Metastable Simulated Body-Fluids on Sol-Gel Prepared Silica.* Biomaterials, 1993. 14(13): p. 963-968.
29. Shikinami, Y. and M. Okuno, *Bioresorbable devices made of forged composites of hydroxyapatite (HA) particles and poly L-lactide (PLLA). Part II: practical properties of miniscrews and miniplates.* Biomaterials, 2001. 22(23): p. 3197-3211.
30. Yong Kang, J. Y., Sadiya Khan, Lucas Anissian. Guillermo A. Ameer *A novel biodegradable elastomers for cartilage tissue engineering.* J Biomed Mater Res, 2006. accepted.

We claim:
1. A composition comprising a composite of:
   a) a polyester consisting of one or more linear aliphatic diol monomers and a citric acid monomer;
   b) a bioceramic used for implantable tissue devices, wherein said composition comprises said bioceramic in an amount of 55% wt % to 75 wt %.
2. The composition of claim 1, wherein the linear aliphatic diol monomer comprises between about 2 and about 20 carbons.
3. The composition of claim 1, wherein the polyester comprises repeating units of the same linear aliphatic diol monomer.
4. The composition of claim 3, wherein the linear aliphatic diol is 1,8-octanediol.
5. The composition of claim 4, wherein the polyester is poly 1,8-octanediol co-citric acid.
6. The composition of claim 3, wherein the polyester is poly 1,10 decanediol co-citric acid.
7. The composition of claim 1, wherein the polyester comprises repeating units of different linear aliphatic diol monomers.
8. The composition of claim 1, wherein said bioceramic is selected from the group consisting of calcium phosphate bioceramics, aluminabased bioceramics; zirconia-based bioceramics; silica-based bioceramics, and pyrolytic carbon-based bioceramics.
9. The composition of claim 8, wherein said bioceramic is a calcium phosphate bioceramic.
10. The composition of claim 9, wherein said bioceramic is hydroxyapatite (HA).
11. The composition of claim 10, wherein said HA is present in an amount of at least 60 wt %.
12. The composition of claim 10, wherein said HA is present in an amount of at least 65 wt %.
13. The composition of claim 5, wherein said composite has a bending strength of from about 33.9 to about 41.4 MPa.
14. The composition of claim 5, wherein said composite has a compression strength of from about 32 to about 75 MPa.
15. The composition of claim 5, wherein said composite has a tensile strength of from about 6 to about 10 MPa.
16. The composition of claim 5, wherein said composite has a shear strength of from about 23 to about 28 MPa.
17. The composition of claim 5, wherein said composite has a bending modulus of from about 0.275 to about 0.502 GPa.
18. An implantable device comprising the composition of claim 1.
19. The composition of claim 1, wherein the bioceramic comprises particles.
20. The composition of claim 19, wherein the particles have a size from a nanometer to a micron.

* * * * *